(12) United States Patent
Moretti

(10) Patent No.: US 9,487,734 B2
(45) Date of Patent: *Nov. 8, 2016

(54) PERFUMING INGREDIENTS OF THE FLORAL AND/OR ANIS TYPE

(71) Applicant: FIRMENICH SA, Geneva 8 (CH)

(72) Inventor: Robert Moretti, Grand-Lancy (CH)

(73) Assignee: Firmenich SA, Geneva (CH)

( * ) Notice: Subject to any disclaimer, the term of this patent is extended or adjusted under 35 U.S.C. 154(b) by 77 days.

This patent is subject to a terminal disclaimer.

(21) Appl. No.: 14/323,594

(22) Filed: Jul. 3, 2014

(65) Prior Publication Data

US 2014/0314699 A1 Oct. 23, 2014

Related U.S. Application Data

(62) Division of application No. 13/123,642, filed as application No. PCT/IB2009/054864 on Nov. 3, 2009, now Pat. No. 8,815,792.

(30) Foreign Application Priority Data

Nov. 7, 2008 (WO) .................. PCT/IB2008/054662

(51) Int. Cl.
| | | |
|---|---|---|
| *C11B 9/00* | (2006.01) | |
| *C07C 69/618* | (2006.01) | |
| *C07C 255/34* | (2006.01) | |
| *C07C 47/232* | (2006.01) | |
| *A61K 8/33* | (2006.01) | |
| *A61K 8/40* | (2006.01) | |
| *A61K 8/37* | (2006.01) | |
| *A61Q 5/00* | (2006.01) | |
| *A61Q 5/02* | (2006.01) | |
| *A61Q 19/00* | (2006.01) | |
| *A61Q 19/10* | (2006.01) | |
| *A61Q 15/00* | (2006.01) | |
| *A61Q 5/06* | (2006.01) | |
| *C07C 33/30* | (2006.01) | |

(52) U.S. Cl.
CPC .............. *C11B 9/0061* (2013.01); *A61K 8/33* (2013.01); *A61K 8/37* (2013.01); *A61K 8/40* (2013.01); *A61Q 5/00* (2013.01); *A61Q 5/02* (2013.01); *A61Q 5/06* (2013.01); *A61Q 15/00* (2013.01); *A61Q 19/00* (2013.01); *A61Q 19/002* (2013.01); *A61Q 19/10* (2013.01); *C07C 33/30* (2013.01); *C07C 47/232* (2013.01); *C07C 69/618* (2013.01); *C07C 255/34* (2013.01); *C11B 9/0065* (2013.01)

(58) Field of Classification Search
None
See application file for complete search history.

(56) References Cited

U.S. PATENT DOCUMENTS

| | | | |
|---|---|---|---|
| 3,862,340 A * | 1/1975 | Schreiber ............ | A23L 1/22657 424/76.4 |
| 3,996,290 A | 12/1976 | Tavares et al. | |
| 4,464,280 A | 8/1984 | Boden et al. | |
| 6,369,110 B1 | 4/2002 | Kitano et al. | |
| 2007/0275987 A1* | 11/2007 | Conte .................. | C07D 471/04 514/264.1 |

FOREIGN PATENT DOCUMENTS

| | | |
|---|---|---|
| WO | 95/30406 A1 | 11/1995 |
| WO | 99/61414 A1 | 12/1999 |

OTHER PUBLICATIONS

Ananda H.B. Herath-Mudlyansela. "Development of Nickel-Catalyzed Cycloaddition and Coupling Reactions" Ph.D. dissertation at the University of Michigan, 2008. p. 39.*
Sylvie Derien and Pierre H. Dixneuf. Ruthenium Catalysed Synthesis of Unsaturated Acetals and Aldehydes via C-C Bond Coupling of Alkynes with Allyl Alcohol. J. Chem. Soc., Chem. Commun., 1994, 2551-2552.*
International Search Report and Written Opinion, PCT/IB2009/054864, Feb. 26, 2010.
Chalk et al., "Palladium-Catalyzed Vinyl Substitution Reactions. II. Synthesis of Aryl Substituted Allylic Alcohols, Aldehydes, and Ketones from Aryl Halides and Unsaturated Alcohols," J. Org. Chem., 41(7):1206-1209.

(Continued)

*Primary Examiner* — Frederick Krass
*Assistant Examiner* — Michael P Cohen
(74) *Attorney, Agent, or Firm* — Winston & Strawn LLP

(57) ABSTRACT

The present invention concerns a compound of formula

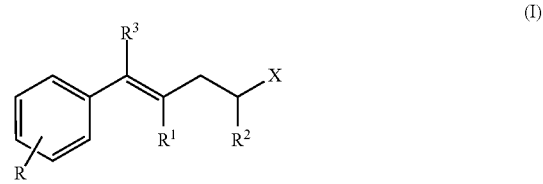

(I)

wherein R represents a hydrogen atom or a $C_{1-2}$ alkyl or alkoxyl group;

each $R^1$, $R^2$ or $R^3$ represents a hydrogen atom or a methyl or ethyl group; and X represents a CHO, COOR$^4$ or CN group, $R^4$ being a methyl or ethyl group; and at least one of said R, $R^1$ or $R^2$ represents a group containing at least one carbon atom;

and it use as perfuming ingredient, for instance to impart odor notes of the floral and/or anis type.

10 Claims, No Drawings

(56) References Cited

OTHER PUBLICATIONS

Chang et al., "Cobalt-Catalyzed Reductive Coupling of Activated Alkenes with Alkynes," J. Am. Chem. Soc., 129:12032-12041 (2007).

Dérien et al., "Ruthenium Catalysed Synthesis of Unsaturated Acetals and Aldehydes via C-C Bond Coupling of Alkynes with Allyl Alcohol," J. Chem. Soc., Chem. Commun., 2551-2552 (1994).

Fujimura et al., "Hydroxyl-Directed, Stereoselective Olefination of Ketones by Transition Metal Alkylidenes," J. Am. Chem. Soc., 117:2355-2356 (1995).

Wang et al., "Cobalt-Catalyzed Highly Regio- and Stereoselective Intermolecular Reductive Coupling of Alkynes with Conjugated Alkenes," J. Am. Chem. Soc., 124:9696-9697 (2002).

Mimosa odor descriptor from the Good Scents Company, downloaded on Jan. 9, 2012, from the site: http://www.thegoodscentscompany.com/odor/mimosa.html.

* cited by examiner

PERFUMING INGREDIENTS OF THE FLORAL AND/OR ANIS TYPE

CROSS-REFERENCE TO RELATED APPLICATIONS

This application is a division of U.S. application Ser. No. 13/123,642 filed Apr. 11, 2011, which is the 371 filing of International Patent Application no. PCT/IB209/054864 filed Nov. 3, 2009, which in turn claims priority to International Application no. PCT/IB2008/054662 filed Nov. 7, 2008.

TECHNICAL FIELD

The present invention relates to the field of perfumery. More particularly, it concerns the use as perfuming ingredient of a compound of formula

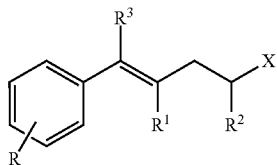
(I)

wherein X represents a CHO, COOR$^4$ or CN group, R$^4$ being a methyl or ethyl group, and at least one of said R, R$^1$ or R$^2$ represents a group containing at least one carbon atom.

The present invention concerns also the use of said compound in the perfumery industry as well as the compositions or articles containing said compound, and some of said compounds.

PRIOR ART

To the best of our knowledge, none of the invention's compounds have been described as perfuming ingredients.

The closest analogues known in the prior art as perfuming ingredients are 3-methyl-5-phenylpentanal and 3-methyl-5-phenyl-1-pentanol (see below). However, said compounds do not possess a carbon-carbon double bond in the chain and have a substitution pattern substantially different, not to mention the fact that the odors are totally different.

One may also cite the compound 5-phenyl-2-pentenal (U.S. Pat. No. 3,862,340), which has a structure close to the one of formula (I). However, this compound is reported only as flavor ingredient, i.e. for totally different use.

Amongst the claimed compounds only 4-methyl-5-phenyl-4-pentenenitrile (see C. C. Wang et al, in *J.A.C.S.*, 2002, 124, 9696), 2,4-dimethyl-5-phenyl-4-pentenal (see C. C. Wang et al, in *J.A.C.S.*, 2007, 129, 12032), 4-methyl-5-phenyl-4-penten-1-ol (see A. J. Chalk, et al, in *J.O.C.* 1976, 41, 1206), 4-methyl-5-phenyl-4-pentenal (see P. H. Dixneuf et al, in *J.C.S. Chem. Commun.* 1994, 2551-2), 4-(phenylmethylene)-1-hexanol (see O. Fujimura et al, in *J.A.C.S.* 1995, 117, 2355), ethyl 4-methyl-5-phenyl-4-pentenoate (see WO 99/61414) are known, and are all reported as simple chemical compounds. None of these prior art documents reports or suggests any organoleptic properties of the compounds of formula (I), or any use of said compounds in the field of perfumery.

DESCRIPTION OF THE INVENTION

We have now surprisingly discovered that a compound of formula

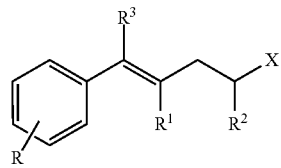
(I)

wherein R is an ortho, meta or para substituent of the phenyl, and represents a hydrogen atom or a $C_{1-2}$ alkyl or alkoxyl group;

R$^1$ represents a hydrogen atom or a $C_{1-3}$ alkyl group;

R$^2$ represents a hydrogen atom or a methyl or ethyl group;

R$^3$ represents a hydrogen atom or a methyl or ethyl group; and

X represents a CHO, COOR$^4$ or CN group, R$^4$ being a methyl or ethyl group; and at least one of said R, R$^1$ or R$^2$ represents a group containing at least one carbon atom, and said compound being in the form of a E or Z isomer or of a mixture thereof;

can be used as perfuming ingredient, for instance to impart odor notes of the floral and/or anis type.

According to a particular embodiment of the invention, said invention's compounds are those wherein at least two of said R, R$^1$ or R$^2$ represents a group containing at least one carbon atom.

According to a particular embodiment of the invention, said compounds (I) are those wherein R is an ortho, meta or para substituent of the phenyl ring and represent a hydrogen atom or a methyl or ethyl group;

R$^1$ represents a methyl or ethyl group;

R$^2$ represents a hydrogen atom or a methyl or ethyl group;

R$^3$ represents a hydrogen atom or a methyl or ethyl group; and

X represents a CHO, COOR$^4$ or CN group, R$^4$ being a methyl or ethyl group.

According to another particular embodiment of the invention, said compounds (I) are those wherein R is an ortho, meta or para substituent of the phenyl ring and represents a hydrogen atom or a methyl or ethyl group;

R$^1$ represents a methyl or ethyl group;

R$^2$ represents a hydrogen atom or a methyl or ethyl group;

R$^3$ represents a hydrogen atom or a methyl or ethyl group; and

X represents a CHO, COOR$^4$ or CN group, R$^4$ being a methyl or ethyl group; and at least one of said R, R$^2$ or R$^3$ represents a methyl or ethyl group, in particular R or R$^3$ represents a methyl or ethyl group.

According to any one of the above embodiments of the invention, said compounds (I) are those wherein X represents a CHO group.

According to any one of the above embodiments of the invention, said compounds (I) are those wherein each R, R$^2$ or R$^3$ represents a hydrogen atom or methyl group, and/or R$^1$ represents a methyl group.

The compounds of formula

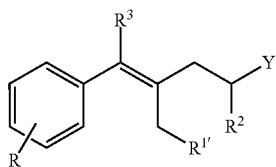

(II)

wherein $R^{1'}$ represents a hydrogen atom or a methyl group, Y represents a $CH_2OH$ group or a group X, and X, R, $R^2$ and $R^3$ have the same meaning as in any one of the above embodiments; said compound being in the form of a E or Z isomer or of a mixture thereof;
are also novel compounds, with the exception of 4-methyl-5-phenyl-4-pentenenitrile, 2,4-dimethyl-5-phenyl-4-pentenal, 4-methyl-5-phenyl-4-penten-1-ol, 4-methyl-5-phenyl-4-pentenal, ethyl 4-methyl-5-phenyl-4-pentenoate and 4-(phenylmethylene)-1-hexanol. The compounds wherein Y is $CH_2OH$ are included as useful intermediates for the preparation of all the other invention's compounds, as it will be seen further below.

Said compound of formula (II) is also another object of the present invention.

Furthermore, since the invention's compounds have a carbon-carbon double bond, said compounds can be in the form of a E or Z isomer or of a mixture thereof. According to any one of the above embodiments of the invention, said compounds (I) or (II) are those which are in the form of mixture of E and Z isomers and the E isomer accounts for at least 75% w/w of said mixture, or even at least 88%, or even at least 95%.

According to any one of the above embodiments of the invention, said compounds (I) or (II) are those wherein the R group is methyl or ethyl group.

According to any one of the above embodiments of the invention, said compounds (I) or (II) are those wherein the R group is a para, meta or ortho substituent, and in particular is a para or meta substituent, or of a mixture thereof. According to any one of the above embodiments of the invention, said compounds (I) are those which are in the form of mixture of para or meta substituent and the para substituent accounts for at least 90% w/w of said mixture, or even at least 95%.

According to a particular embodiment of the invention, said invention's compounds of formula (I) or (II) are those having 13 or 14 carbon atoms in total.

As specific examples of the invention's compounds, one may cite, as non-limiting example, (4E)-4-methyl-5-(4-methylphenyl)-4-pentenal, which possesses a very nice lily of the valley note together with powdery-anisic notes, as well as watery aspects, almost a perfume on its own. The odor of this compound can be also described as having an elegant lily of the valley/mimosa duality. The overall odor reminds of the known ingredient 3-(4-isopropylphenyl)-2-methylpropanal.

As other example one may cite (4E)-2,4-dimethyl-5-(4-methylphenyl)-4-pentenal, which in addition to the lily of the valley and powdery-anis note possesses also aldehydic notes as well as natural almond and creamy aspects, with bottom notes reminding of linden or verbena.

As other specific, but non-limiting, examples of the invention's compounds, one may cite the following ones in Table 1:

TABLE 1

Invention's compounds and their odor properties

| Compound structure and name | Odor |
|---|---|
| (4E)-4-methyl-5-(3-methylphenyl)-4-pentenal | Compared to its para isomer described above, this compound differentiates himself by being less mimosa and powdery, although being overall more powerful |
| 4-methyl-5-phenyl-4-hexenal | Lily of the valley, very floral, with a sweet and slightly smoked aspect, possesses a good radiance |
| 2,4-dimethyl-5-phenyl-4-pentenal | Linden, watery, aldehydic odor |
| 2-ethyl-4-methyl-5-(4-methylphenyl)-4-pentenal | Lily of the valley, anisic odor |

TABLE 1-continued

| Invention's compounds and their odor properties | |
|---|---|
| Compound structure and name | Odor |
| 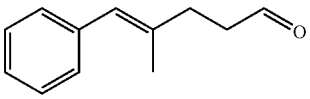<br>4-methyl-5-phenyl-4-pentenal | Powerful and nice lily of the valley, green, aldehydic odor |
| 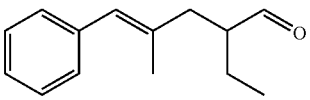<br>2-ethyl-4-methyl-5-phenyl-4-pentenal | Watery, aldehydic, lily of the valley odor |
| 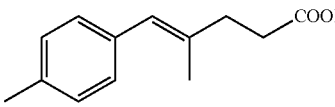<br>Methyl (4E)-4-methyl-5-(4-methylphenyl)-4-pentenoate | Benzoic, orange flower, mimosa, anis, natural odor |
| 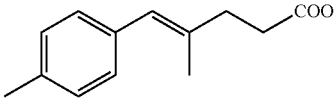<br>Ethyl (4E)-4-methyl-5-(4-methylphenyl)-4-pentenoate | Anisic, lily of the valley odor |
| 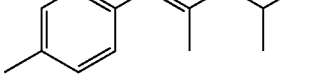<br>Methyl (4E)-2,4-dimethyl-5-(4-methylphenyl)-4-pentenoate | Mimosa, anisic, amaretti odor |
| 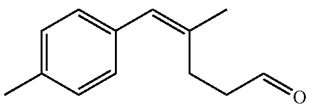<br>(4Z)-4-methyl-5-(4-methylphenyl)-4-pentenal | Similar to its isomer (4E)-4-methyl-5-(4-methylphenyl)-4-pentenal, but possessing also an aldehydic and cherry note |
| 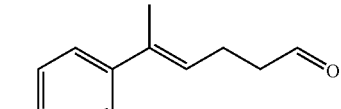<br>(4E)-5-(4-methylphenyl)-4-hexenal | Floral, aldehydic |
| 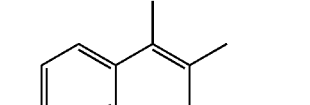<br>(Z)-4-methyl-5-p-tolylhex-4-enal | Similar to (4E)-4-methyl-5-(4-methylphenyl)-4-pentenal, but possessing also an aldehydic note |

TABLE 1-continued

Invention's compounds and their odor properties

| Compound structure and name | Odor |
|---|---|
| 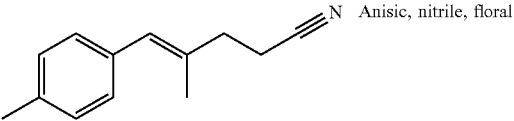<br>(E)-4-methyl-5-p-tolylpent-4-enenitrile | Anisic, nitrile, floral |

According to a particular embodiment of the invention, the compounds of formula (I) are: (4E)-4-methyl-5-(4-methylphenyl)-4-pentenal, (4E)-2,4-dimethyl-5-(4-methylphenyl)-4-pentenal, 2,4-dimethyl-5-phenyl-4-pentenal, 4-methyl-5-phenyl-4-hexenal, 4-methyl-5-phenyl-4-pentenal or methyl (4E)-4-methyl-5-(4-methylphenyl)-4-pentenoate.

As can be seen, from the above table, although the precise tonalities of the invention's compounds may vary according to the exact structure of the compounds, the invention's compounds are characterized by floral notes, and in particular notes of the lily of the valley, mimosa and/or anisic type, frequently together with watery and/or powdery aspect.

This combination of lily/mimosa/anis characters is typical of the invention's compounds odors and distinguish said compounds from those of the prior art having a similar structure and being known as perfuming ingredients. Indeed, Mefranal® (3-methyl-5-phenylpentanal from Quest) is characterized by a typical lemon, citronella odor, absent from the invention's compounds, while 3-methyl-5-phenyl-1-pentanol (Arctander N° 2200) is characterized by an herbaceous, dry odor with woody undernotes, which is also very different from the odor of the present compounds (I).

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids : Stabilisatoren, Dickungs-und Gehermittel in Lebensmittel, Band 2 der Schriftenreihe Lebensmittelchemie, Lebensmittelqualität, Behr's Verlag-GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product, could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I), as defined above, or an invention's perfuming composition; and
ii) a consumer product base;
is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric softeners, fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. Concentrations lower than these, such as in the order of 0.01% to 1% by weight, can be used when these compounds are incorporated into perfumed articles, percentage being relative to the weight of the article.

The invention's compounds can be prepared according to a method comprising the preparation of an ester of the invention, which can be converted into an alcohol by reduction, and finally the oxidation of said alcohol into an invention's aldehyde. The alcohol and the aldehyde can be subsequently be transformed into an ether, acetal or cyanide according to the invention using standard methods known from the art. The ester itself can be prepared by reacting an appropriate orthoester with an appropriate allyl-benzyl alcohol, under Claisen rearrangement conditions, as show in the scheme herein below:

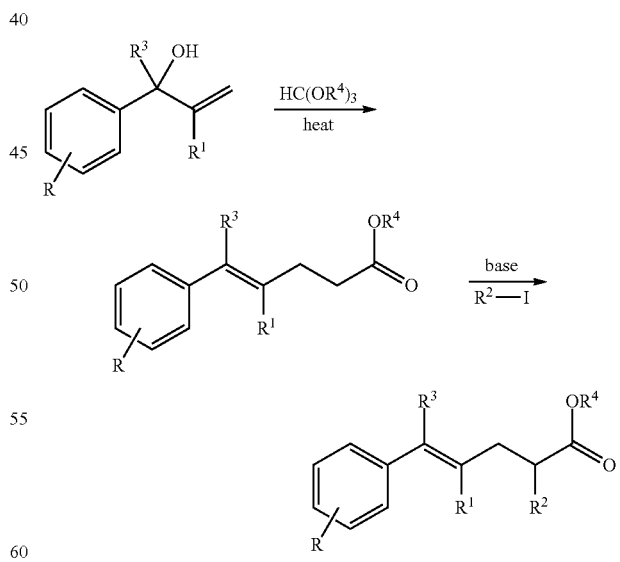

Using such methodology, the alcohols and esters according to the invention are also valuable intermediates for the production of the aldehydes and cyanides of formula (I).

Alternatively, the invention's compounds can be obtained by a process comprising the following key steps:

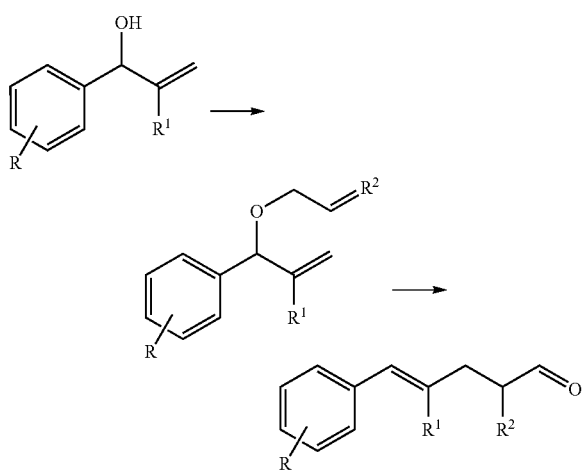

The aldehyde can be then transformed into the desired invention's compound using standard methods.

Other methods for the production of the aldehydes (I) are also possible, as described in the Examples.

Examples of all said methodologies are provided herein below in the Examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)
Methyl (4E)-4-methyl-5-(4-methylphenyl)-4-pentenoate Trimethyl orthoacetate (273 g, 2.24 mol) and 1-(4-methylphenyl)-2-methyl-2-propen-1-ol (91.4% pure, 39.92 g, 0.224 mol) were heated in the presence of propionic acid (0.5 ml) in an oil bath at 120°-150° C. The methanol formed during the reaction was distilled first, followed by the excess orthoacetate. The product was then freed from residual orthoacetate under vacuum and purified by column chromatography on silica gel (eluent: heptanes/ethyl acetate 25:1 to 5:1), followed by bulb-to-bulb distillation (100° C./0.001 mbar). 19.62 g (yield=40%) of the desired product were obtained.

$^{13}C$-NMR: 173.66 (s), 136.24 (s), 135.68 (s), 135.25(s), 128.76 (d), 128.73 (d), 125.75 (d), 51.56 (q), 35.67 (t), 33.00 (t), 21.11 (q), 17.64 (q).

$^1H$-NMR: 7.10 (s, 4H), 6.25 (s, 1H), 3.68 (s, 3H), 2.55-2.45 (m, 4H), 2.32 (s, 3H), 1.87 (s, 3H).

(4E)-4-Methyl-5-(4-methylphenyl)-4-penten-1-ol

A solution of methyl (4E)-4-methyl-5-(4-methylphenyl)-4-pentenoate (17.18 g, 0.079 mol) in dry THF (300 ml) was treated, at −78° C. under nitrogen, with solid lithium aluminum hydride (3.15 g, 0.079 mol) in one portion. After 5 minutes the cooling bath was removed and the reaction allowed to reach room temperature and then cooled to 0° C. and treated successively with water (3.15 ml), 5% aqueous sodium hydroxide (9.45 ml) and water (3.15 ml). The reaction was stirred at room temperature for 30 minutes. Anhydrous solid sodium sulfate was added (10 g) and stirring continued for 5 minutes. The solid was filtered off, rinsed with diethyl ether and solvents were removed under vacuum. The product was purified by column chromatography on silica gel (eluent: heptanes/ethyl acetate 5:1 to 1:1) followed by bulb-to-bulb distillation (120° C./0.001 mbar). 12.54 g (yield=66%) of the desired product were obtained.

$^{13}C$-NMR: 137.75 (s), 135.50 (s), 135.48 (s), 128.74 (d), 128.69 (d), 125.06 (d), 62.55 (t), 36.97 (t), 30.91 (t), 21.10 (q), 17.73 (q).

1H-NMR: 7.12 (s, 4H), 6.25 (broad s, 1H), 3.65 (q, J=6, 2H), 2.32 (s, 3H), 2.22 (t, J=7, 2H), 2.04 (t, J=6, 1H), 1.86 (s, 3H), 1.78 (m, 2H).

(4E)-4-methyl-5-(4-methylphenyl)-4-pentenal

Solid pyridinium chlorochromate (13.2 g, 0.06 mol) was added in one portion to a pre-cooled (−10° C.) solution of (4E)-4-Methyl-5-(4-methylphenyl)-4-penten-1-ol (9.88 g, 0.052 mol) in dry dichloromethane (250 ml) under nitrogen. After 30 minutes, the reaction was warmed up to room temperature. After 1 hour, diethyl ether (700 ml) was added to the reaction. After stirring for 10 minutes, the reaction was filtered through silica gel, rinsing with diethyl ether. The solvent was removed under vacuum and the residue was purified by column chromatography on silica gel (eluent: heptanes/ethyl acetate 10:1) followed by bulb-to-bulb distillation (100° C./0.001 mbar). 3.55 g (yield=36%) of the desired product were obtained.

$^{13}C$-NMR: 202.10 (d), 135.96 (s), 135.78 (s), 135.06 (s), 128.78 (d), 128.70 (d), 125.67 (d), 42.24 (t), 32.75 (t), 21.11 (q), 17.82 (q).

$^1H$-NMR: 9.80 (t, J=2.5, 1 H), 7.12 (s, 4H), 6.35 (s, 1H), 2.62 (td, $J_d$=2.5, $J_t$=7, 2H), 2.49 (t, J=7, 2H), 2.32 (s, 3H), 1.86 (s, 3H).

Methyl (4E)-4-methyl-5-phenyl-4-pentenoate

Trimethyl orthoacetate (186 g, 1.52 mol) and 1-phenyl-2-methyl-2-propen-1-ol (90% pure from Alfa Aesar, 25 g, 0.152 mol) were heated in the presence of propionic acid (0.2 ml) in an oil bath at 145° C. for 4 hours. The methanol formed during the reaction was distilled. The excess orthoacetate was then removed under vacuum and the residue was purified by column chromatography on silica gel (eluent: heptanes/ethyl acetate 25:1 to 8:1) followed by bulb-to-bulb distillation (67° C./0.001 mbar). 6.5 g (yield=21%) of the desired product were obtained.

$^{13}C$-NMR: 173.61 (s), 138.15 (s), 136.99 (s), 128.82 (d), 128.05 (d), 126.10 (d), 125.69 (d), 51.58 (q), 35.61 (t), 32.95 (t), 17.64 (q).

$^1H$-NMR: 7.33-7.28 (m, 2H), 7.25-7.15 (m, 3H), 6.29 (s, 1H), 3.69 (s, 3H), 2.57-2.46 (m, 4H), 1.86 (s, 3H).

(4E)-4-methyl-5-phenyl-4-penten-1-ol

A solution of methyl (4E)-4-methyl-5-phenyl-4-pentenoate (3.5 g, 0.016 mol) in dry THF (100 ml) was treated, at −78° C. under nitrogen, with solid lithium aluminum hydride (1 g, 0.025 mol) in one portion. After 5 minutes, the cooling bath was removed and the reaction allowed reaching room temperature and then cooled to 0° C. and treated successively with water (1 ml), 5% aqueous sodium hydroxide (3 ml) and water (1 ml). The reaction was stirred at room temperature for 30 minutes. Anhydrous solid sodium sulfate was added (3 g) and stirring continued for 5 minutes. The solid was filtered off, rinsed with diethyl ether and the filtrate was evaporated under vacuum. The product was purified by bulb-to-bulb distillation (84° C./0.002 mbar). 2.88 g (yield=100%) of the desired product were obtained.

¹³C-NMR: 138.49 (s), 138.40 (s), 128.79 (d), 128.17 (d), 125.92 (d), 125.20 (d), 62.52 (t), 36.92 (t), 30.89 (t), 17.74 (q).

¹H-NMR: 7.32-7.27 (m, 2H), 7.25-7.14 (m, 3H), 6.29 (s, 1H), 3.67 (t, J=7, 2H), 2.24 (t, J=7, 2H), 2.05 (s, 1H), 1.86 (s, 3H), 1.78 (m, 2H).

(4E)-4-methyl-5-phenyl-4-pentenal

Solid pyridinium chlorochromate (4.21 g, 0.02 mol) was added in one portion to a cooled (−10° C.) solution of (4E)-4-methyl-5-phenyl-4-penten-1-ol (2.25 g, 0.013 mol) in dry dichloromethane (50 ml) under nitrogen. After 30 minutes, the reaction was warmed up to room temperature. After 1 hour, diethyl ether (250 ml) was added to the reaction. After stirring for 10 minutes, the reaction was filtered through silica gel and the solid rinsed with diethyl ether. The solvent was removed under vacuum and the residue was purified by column chromatography on silica gel (eluent: heptanes/ethyl acetate 25:1) followed by bulb-to-bulb distillation (82° C./0.002 mbar). 1.21 g (yield=53%) of the desired product was obtained.

¹³C-NMR: 201.98 (d), 137.97 (s), 136.71 (s), 128.80 (d), 128.08 (d), 126.17 (d), 125.81 (d), 42.19 (t), 32.68 (t), 17.82 (q).

¹H-NMR: 9.70 (d, J=2.5, 1H), 7.32-7.27 (m, 2H), 7.24-7.17 (m, 3H), 6.29 (s, 1H), 2.68-2.60 (m, 2H), 2.53-2.47 (m, 2H), 1.86 (s, 3H).

Ethyl (4E)-4-methyl-5-(4-methylphenyl)-4-pentenoate 1-(4-methylphenyl)-2-methyl-2-propen-1-ol (64.9 g, 0.4 mol) and triethyl orthoacetate (335 g, 2 mol) were heated in the presence of propionic acid (0.5 ml) in an oil bath at 150° C. (the ethanol formed during the reaction distills during this period) for 3 hours, then progressively to 200° C. (to distill off the excess orthoacetate). The product was then distilled under high vacuum (105° C./0.001 mbar) through a 20-cm Widmer column. 21.5 g of the desired product were obtained (94% purity, yield=24%).

¹³C-NMR: 173.23 (s), 136.30 (s), 135.65 (s), 135.27 (s), 128.75 (d), 128.72 (d), 125.5 (d), 60.34 (t), 35.31 (t), 33.23 (t), 21.11 (q), 17.65 (q), 14.29 (q).

¹H-NMR: 7.10 (s, 4H), 6.25 (s, 1H), 3.63 (q, J=7, 2H), 2.50 (m, 4H), 2.32 (s, 3H), 1.86 (s, 3H), 1.25 (t, J=7, 3H).

Ethyl (4E)-2,4-dimethyl-5-(4-methylphenyl)-4-pentenoate n-Butyl lithium (1.6 M in hexanes from Fluka, 70 ml, 0.111 mol) was added rapidly to a solution of diisopropylamine (11.7 g, 0.116 mol) in dry THF (200 ml) under nitrogen, maintaining the temperature below −20° C. by cooling in a dry ice-acetone bath. After cooling to −78° C., dry DMPU (14.9 g, 0.116 mol) was added drop-wise for 5 minutes. Then, ethyl (4E)-4-methyl-5-(4-methylphenyl)-4-pentenoate (21.5 g, 0.092 mol) was added in 10 minutes. The reaction was warmed up to 0° C. and kept for 20 minutes at this temperature before cooling back to −78° C. Methyl iodide (66 g, 0.46 mol) was added drop-wise. The reaction was warmed up to room temperature and stirred overnight. It was then poured onto water and extracted twice with diethyl ether. Each organic fraction was washed with water and brine. Combined extracts are dried over solid anhydrous sodium sulfate. The solid was filtered off, rinsed with diethyl ether. Solvents are removed under vacuum and the product was purified by bulb-to-bulb distillation (125° C./0.04 mbar). 18.5 g of colorless liquid were obtained (yield=81%).

¹³C-NMR: 176.40 (s), 135.67 (s), 135.28 (s), 135.17 (s), 128.78 (d), 128.73 (d), 127.07 (d), 60.22 (t), 45.04 (t), 38.19 (d), 21.12 (q), 17.53 (q), 16.75 (q), 14.30 (q).

¹H-NMR: 7.12 (s, 4H), 6.25 (s, 1H), 3.63 (q, J=7, 2H), 2.72 (m, 1H), 2.53 (m, 1H), 2.32 (s, 3H), 2.21 (m, 1H), 1.83 (s, 3H), 1.23 (t, J=7, 3H), 1.17 (d, J=7, 3H).

Methyl (4E)-2,4-dimethyl-5-(4-methylphenyl)-4-pentenoate

A solution of sodium hydroxide (7.8 g, 0.195 mol) in water (25 ml) was added to a solution of ethyl (4E)-2,4-dimethyl-5-(4-methylphenyl)-4-pentenoate (16 g, 0.065 mol) in ethanol (70 ml) at room temperature. The reaction was stirred overnight before removing ethanol under vacuum. Water (200 ml) was added to the residue which was washed twice with diethyl ether. Each organic phase was treated with water. Combined aqueous phases were treated with 5% aqueous HCl (150 ml). The resulting solution was extracted twice with diethyl ether. Each organic fraction was washed with water and brine, before being combined and dried over solid anhydrous sodium sulfate. The solid was filtered off, rinsed with diethyl ether. The solvent was removed to a obtain a crude carboxylic acid.

The crude acid was dissolved in absolute methanol (250 ml) under nitrogen. Acetyl chloride (11 g, 0.142 mol) was added drop-wise without external cooling (exothermic). After 4 hours, solvents were removed under vacuum and the product was directly chromatographed on silica gel (eluent: heptanes/ethyl acetate 25:1 to 5:1). Bulb-to-bulb distillation (123° C./0.065 mbar) gives the desired methyl ester (8.4 g, yield=56%).

¹³C-NMR: 176.86 (s), 135.72 (s), 135.25 (s), 135.10 (s), 128.75 (d), 128.72 (d), 127.14 (d), 51.54 (q), 45.00 (t), 38.14 (d), 21.12 (q), 17.49 (q), 16.67 (q).

¹H-NMR: 7.11 (s, 4 H), 6.25 (s, 1 H), 3.65 (s, 3 H), 2.73 (m, 1 H), 2.54 (m, 1 H), 2.32 (s, 3 H), 2.23 (m, 1 H), 1.82 (s, 3 H), 1.18 (d, J=7 Hz, 3 H).

1-[1-(Allyloxy)-2-methyl-2-propenyl]-4-methylbenzene

Solid sodium tert-butylate (66.65 g, 0.589 mol) was dissolved under nitrogen in dry THF (350 ml) and 1-(4-methylphenyl)-2-methyl-2-proper-1-ol (41.16 g, 0.239 mol) in dry THF (25 ml) was added in 15 minutes without external cooling. The reaction was further stirred at room temperature for 50 minutes. Tetra butyl ammonium iodide (5.04 g, 0.014 mol) was added followed by allyl chloride (40 g, 0.518 mol) in 25 minutes (exothermic to 47° C.). The reaction was stirred for 24 hours, before adding more tetra butyl ammonium iodide (2.30 g, 0.006 mol) and allyl chloride (9.30 g, 0.120 mol). After stirring for 24 hours at room temperature, the reaction was poured onto ice, diluted with MTBE and acidified with aqueous phosphoric acid. The organic phase was washed with brine, saturated aqueous sodium bicarbonate and brine and dried over solid anhydrous sodium sulfate. The solid was filtered off, rinsed with MTBE and solvents were removed under vacuum. The product was purified by distillation through a 35-cm Fisher column. 38.78 g of the desired allyl ether were obtained (yield=80%). B.P.=79° C./1.6 mbar ¹³C-NMR: 145.26 (s), 137.57 (s), 136.91 (s), 135.00 (d), 128.84 (d), 126.61 (d), 116.44 (t), 112.58 (t), 84.20 (d), 69.13 (t), 21.12 (q), 17.74 (q).

¹H-NMR: 7.18 (m, 4H), 5.98-5.88 (m, 1H), 5.30 (m, 1H), 5.15 (m, 1H), 5.12 (m, 1H), 4.94 (m, 1H), 4.72 (s, 1H), 4.02-3.90 (m, 2H), 2.32 (s, 3H), 1.58 (s, 3H).

(4E)-2,4-dimethyl-5-(4-methylphenyl)-4-pentenal

The 1-[1-(allyloxy)-2-methyl-2-propenyl]-4-methylbenzene (24 g, 0.116 mol) and [RuCl$_2$(PPh$_3$)$_3$] (200 mg) were heated in the presence of BHT (50 mg) in pseudo-cumene (50 ml) at 170-180° C. (reflux) for 4 hours.

After cooling to room temperature, the solvent was removed under vacuum and the residue purified by column chromatography on silica gel (eluent: heptanes/ethyl acetate 25:1) followed by fractional distillation using a 20-cm Widmer column. 5 g of the desired aldehyde were obtained (yield=21%). P.P.=73° C./0.12 mbar ¹³C-NMR: 204.73 (d), 135.86 (s), 135.00 (s), 134.38 (s), 128.79 (d), 128.72 (d), 127.57 (d), 44.59 (d), 41.70 (t), 21.11 (q), 17.66 (q), 13.16 (q).

¹H-NMR: 9.68 (d, J=2.5, 1H), 7.12 (s, 4H), 6.27 (s, 1H), 2.67-2.57 (m, 2H), 2.32 (s, 3H), 2.14 (m, 1H), 1.85 (s, 3H), 1.11 (d, J=7, 3H).

1-[1-(2-Butenyloxy)-2-methyl-2-propenyl]-4-methylbenzene

Solid potassium tert-butylate (47 g, 0.411 mol) was added portion-wise (ca 15 min.) to a solution of 1-(4-methylphenyl)-2-methyl-2-propen-1-ol (96% pure, 46.27 g, 0.274 mol) in dry THF (500 ml) at room temperature under nitrogen (exothermic to 30° C.). After 1 more hour at room temperature, the reaction was cooled to 5° C. and tetra butyl ammonium iodide (5.2 g, 0.014 mol) was added followed by crotyl chloride (74.4 g, 0.822 mol) drop-wise. The reaction was warmed up to room temperature overnight and poured onto water (800 ml). The reaction was extracted twice with ethyl acetate. Each organic phase was washed with water and brine. Combined extracts were dried over solid anhydrous sodium sulfate. The solid was filtered off, rinsed with diethyl ether and the solvents were removed under vacuum. The product was purified by distillation under vacuum through a 20-cm Widmer column. A 3:1 mixture of E/Z isomers was obtained (96% pure, 57.58 g, yield=93%). B.P.=74° C./0.005 mbar ¹³C-NMR (E-isomer): 145.38 (s), 137.73 (s), 136.82 (s), 128.81 (d), 127.84 (d), 127.51 (d), 126.65 (d), 112.52 (t), 84.01 (d), 68.97 (t), 21.11 (q), 17.80 (q), 13.23 (q).

¹H-NMR: 7.18 (m, 4H), 5.72-5.55 (m, 2H), 5.10 (s, 1H), 4.92 (m, 1H), 4.70 (s, 1H), 4.08-3.80 (m, 2H), 2.32 (s, 3H), 1.70 (m, 3H), 1.55 (s, 3H).

2-Ethyl-4-methyl-5-(4-methylphenyl)-4-pentenal

The 1-[1-(2-butenyloxy)-2-methyl-2-propenyl]-4-methylbenzene (50.12 g, 0.232 mol), [RuCl$_2$(PPh$_3$)$_3$] (400 mg), BHT (50 mg) and pseudo-cumene (60 ml) were heated together in an autoclave placed in an oil bath at 180° C. for 5 hours. After cooling to room temperature, the pseudo-cumene was distilled off (40° C./5 mbar) and the residue chromatographed on silica gel (eluent: heptanes/ethyl acetate 50:1 to 25:1), then distilled under vacuum through a 20-cm Widmer column. 18.1 g of the desired product were obtained (yield=36%). B.P.=80 ° C./0.001 mbar ¹³C-NMR: 204.97 (d), 135.84 (s), 135.01 (s), 134.62 (s), 128.90 (d), 128.78 (d), 127.36 (d), 51.51 (d), 39.91 (t), 21.82 (t), 21.11 (q), 17.82 (q), 11.47 (q).

¹H-NMR: 9.62 (d, J=2.5, 1 H), 7.12 (s, 4H), 6.27 (s, 1H), 2.55-2.37 (m, 2H), 2.32 (s, 3H), 2.25 (m, 1H), 1.80 (s, 3H), 1.72-1.40 (m, 2H), 0.95 (t, J=7, 3H).

[1-(2-Butenyloxy)-2-methyl-2-propenyl]benzene

Solid potassium tert-butylate (26 g, 0.228 mol) was added portion-wise (ca 15 min.) to a solution of 1-phenyl-2-methyl-2-propen-1-ol (90% pure from Alfa Aesar, 25 g, 0.152 mol) in dry THF (300 ml) at room temperature under nitrogen (exothermic to 30° C.). After 1 more hour at room temperature, the reaction was cooled to 5° C. and tetra butyl ammonium iodide (2.9 g, 0.08 mol) was added followed by crotyl chloride (41.3 g, 0.456 mol) drop-wise. The reaction was warmed up to room temperature overnight and poured onto water (500 ml). The reaction was extracted twice with ethyl acetate. Each organic phase was washed with water and brine. Combined extracts were dried over solid anhydrous sodium sulfate. The solid was filtered off, rinsed with diethyl ether and the solvents were removed under vacuum. After column chromatography on silica gel (eluent: heptanes/ethyl acetate 25:1) the product was purified by bulb-to-bulb distillation (100° C./0.001 mbar). A 3:1 mixture of E/Z isomers was obtained (95% pure, 26.78 g, yield=83%).

¹³C-NMR (E-isomer): 145.26 (s), 140.73 (s), 128.93 (d), 128.10 (d), 127.76 (d), 127.16 (d), 126.67 (d), 112.86 (t), 84.14 (d), 69.01 (t), 17.80 (q), 17.68 (q).

1H-NMR: 7.37-7.20 (m, 5 H), 5.75-5.55 (m, 2 H), 5.12 (s, 1 H), 4.95 (m, 1 H), 4.75 (s, 1 H), 4.10-3.80 (m, 2 H), 1.70 (m, 3 H), 1.62-1.55 (m, 3 H).

2-Ethyl-4-methyl-5-phenyl-4-pentenal

The [1-(2-butenyloxy)-2-methyl-2-propenyl]benzene (26.9 g, 0.126 mol), [RuCl$_2$(PPh$_3$)$_3$] (280 mg), BHT (100 mg) and pseudo-cumene (25 ml) were heated together in an autoclave placed in an oil bath at 180° C. for 4 hours. After cooling to room temperature, the pseudo-cumene was distilled off (40° C./5 mbar) and the residue purified by column chromatography on silica gel (eluent: heptanes/ethyl acetate 50:1 to 10:1) followed by bulb-to-bulb distillation (87° C./0.008 mbar). 13.0 g of the desired product were obtained (yield=51%) as a 9:1 mixture of E/Z isomers.

¹³C-NMR (E isomer): 204.91 (d), 137.89 (s), 135.39 (s), 128.82 (d), 128.07 (d), 127.47 (d), 126.22 (d), 51.47 (d), 39.83 (t), 21.82 (t), 17.81 (q), 11.46 (q).

¹H-NMR: 9.62 (d, J=2.5, 1H), 7.32-7.27 (m, 2H), 7.23-7.13 (m, 3H), 6.30 (s, 1H), 2.57-2.37 (m, 2H), 2.28 (m, 1H), 1.85 (s, 3H), 1.73-1.40 (m, 2H), 0.95 (t, J=7, 3H).

(1E)-[3-(allyloxy)-2-methyl-1-propenyl]benzene

Solid potassium tert-butylate (110 g, 0.960 mol) was added portion-wise (1 hour) to a solution of trans-2-methyl-3-phenyl-2-propen-1-ol (100 g, 0.950 mol) in dry THF (1 liter) at room temperature under nitrogen. After 1 more hour at room temperature, the reaction was cooled to 5° C. and tetra butyl ammonium iodide (12.1 g, 0.032 mol) was added followed by allyl chloride (100 g, 1.280 mol) drop-wise. The reaction was warmed up to room temperature overnight and poured onto water (2 liters). The reaction was extracted twice with ethyl acetate. Each organic phase was washed with water and brine. Combined extracts are dried over solid anhydrous sodium sulfate. The solid was filtered off, rinsed with diethyl ether and the solvents were removed under vacuum. The product was purified by distillation through a 20-cm Widmer column. 120.5 g of the desired compound was obtained (97% pure, 0.620 mol, 97%). B.P.=70° C./0.067 mbar.

¹³C-NMR: 137.56 (s), 135.14 (s), 134.86 (d), 128.90 (d), 128.09 (d), 126.84 (d), 126.42 (d), 116.93 (t), 76.21 (t), 70.84 (t), 15.47 (q).

¹H-NMR: 7.32-7.15 (m, 5H), 6.52 (s, 1H), 6.02-5.90 (m, 1H), 5.30 (m, 1H), 5.20 (m, 1H), 4.02-3.98 (m, 4H), 1.89 (s, 3H).

(4E)-2,4-dimethyl-5-phenyl-4-pentenal

The (1E)-[3-(allyloxy)-2-methyl-1-propenyl]benzene (107.79 g, 0.571 mol), [RuCl$_2$(PPh$_3$)$_3$] (3.13 g), BHT (1 g) and benzene (500 ml) were heated together in an autoclave in an oil bath at 190° C. for 4 hours. After cooling to room temperature, solvents were evaporated and the product purified by column chromatography on silica gel (eluent: heptanes/ethyl acetate 10:1) followed by bulb-to-bulb distillation (88° C./0.009 mbar) to give 11.21 g of the desired compound (0.060 mol, 10%).

¹³C-NMR: 204.65 (d), 137.90 (s), 135.16 (s), 128.82 (d), 128.09 (d), 127.68 (d), 126.25 (d), 44.56 (d), 41.63 (t), 17.66 (q), 13.18 (q).

¹H-NMR: 9.67 (d, J=2.5, 1H), 7.32-7.26 (m, 2H), 7.23-7.15 (m, 3H), 6.32 (s, 1H), 2.66-2.58 (m, 2H), 2.18-2.10 (m, 1H), 1.83 (s, 3H), 1.10 (d, J=7, 3H).

2-Methyl-1-(3-methylphenyl)-2-propen-1-ol

3-Methylbenzaldehyde (Aldrich 97%, 62 g, 0.5 mol) was added drop-wise over 1 hour to a commercial solution of 2-propenyl magnesium bromide in THF (Aldrich 0.5 N, 800 ml, 0.4 mol), at −78° C. under nitrogen. The cooling bath was removed and the reaction stirred for 5 hours, before being cooled to 0° C. A saturated aqueous solution of ammonium chloride (300 ml) was added drop-wise at such a rate that the temperature was kept below 20° C. Diethyl ether (600 ml) was then added and the reaction was transferred to a separating funnel. After shaking vigorously, the phases were separated. The organic phase was washed with water and saturated aqueous sodium bicarbonate. Each aqueous phase was re-extracted with diethyl ether. The organic fractions were combined and dried over solid anhydrous sodium sulfate. The solid was filtered off, rinsed with diethyl ether and the solvents were removed under vacuum. The product was purified by column chromatography on silica gel (eluent: heptanes/ethyl acetate 5:1) followed by distillation through a 20-cm Widmer column. 33 g of the desired product were obtained (yield=51%). B.P.=55° C./0.009 mbar $^{13}$C-NMR: 146.89 (s), 141.99 (s), 137.99 (s), 128.38 (d), 128.26 (d), 127.13 (d), 123.59 (d), 110.98 (t), 77.83 (d), 21.42 (q), 18.32 (q).

$^1$H-NMR: 7.23-7.05 (m, 4H), 5.18 (s, 1H), 5.03 (s, 1H), 4.92 (s, 1H), 2.32 (s, 3H), 2.20 (broad s, 1H), 1.47 (s, 3H).

(4E)-4-methyl-5-(3-methylphenyl)-4-pentenal

The 2-methyl-1-(3-methylphenyl-2-propen-1-ol (17.74 g, 0.109 mol), tri(ethylene glycol) divinyl ether (Aldrich 98%, 22.5 g, 0.109 mol) and mercury(II) acetate (1.05 g, 0.003 mol) were heated together under nitrogen at 155-160° C. (bath temperature) for 16 h. After cooling to room temperature, the reaction was diluted with heptanes, washed with water (3 times). Each aqueous phase was re-extracted with heptanes. Combined extracts were dried over solid anhydrous sodium sulfate. The solid was filtered off, rinsed with heptanes and the solvent was removed under vacuum. The crude product was distilled using a Kügelrohr (140° C./0.001 mbar). The distillate was purified by column chromatography on silica gel (eluent: heptanes/ethyl acetate (10:1 to 5:1) followed by bulb-to-bulb distillation (71° C./0.002 mbar). 5.41 g of the desired product were obtained (yield=26%) as an 85:15 mixture of E/Z isomers.

$^{13}$C-NMR (E isomer): 201.95 (d), 137.93 (s), 137.57 (s), 136.50 (s), 129.57 (d), 127.98 (d), 127.06 (d), 125.92 (d), 125.86 (d), 42.26 (t), 32.72 (t), 21.42 (q), 17.84 (q).

$^1$H-NMR (E isomer): 9.81 (t, J=2.5, 1H), 7.22-7.17 (m, 1H), 7.03-6.92 (m, 3H), 6.25 (s, 1H), 2.65-2.46 (m, 4H), 2.32 (s, 3H), 1.85 (s, 3H).

ethyl (4E)-5-(4-methylphenyl)-4-hexenoate

Prepared as described for ethyl (4E)-4-methyl-5-(4-methylphenyl)-4-pentenoate using the following reagents:
2-(4-methyl-l-phenyl)-3-buten-2-ol (0.093 mol)
Triethylorthoacetate (154 g; 0.93 mol)
Propionic acid (0.5 ml).

The product was purified by column chromatography on silica gel (eluting with heptane/ethyl acetate 5:1) followed by bulb-to-bulb distillation. 4.4 g of product were obtained (0.019 mol, 20%).
B.p.=100° C./0.001 mbar 13C-NMR: 173.19 (s); 140.79 (s); 136.37 (s); 135.96 (s); 128.86 (d); 125.55 (d); 125.26 (d); 60.32 (t); 34.28 (t); 24.34 (t); 21.00 (q); 15.83 (q); 14.27 (q)

1H-NMR: 7.20 (m, 4H); 5.68 (m, 1H); 4.12 (q, J=7 Hz, 2H); 2.55-2.40 (m, 4H); 2.32 (s, 3H); 2.05 (s, 3H); 1.22 (t, J=7 Hz, 3H)

(4E)-5-(4-methylphenyl)-4-hexen-1-ol

Prepared as described for (4E)-4-methyl-5-(4-methylphenyl)-4-penten-1-ol using the following reagents:
ethyl (4E)-5-(4-methylphenyl)-4-hexenoate: 4.4 g (0.019 mol)
Lithium aluminium hydride: 95% pure; 1.2 g (0.03 mol)
The product was purified by bulb-to-bulb distillation. 3.4 g of desired alcohol were obtained (0.017 mol; 89% yield).
B.p.=140° C./0.001 mbar $^{13}$C-NMR: 140.95 (s); 136.22 (s); 135.17 (s); 128.96 (d); 128.86 (d); 126.77 (d); 125.64 (d); 125.47 (d); 62.53 (t); 32.59 (t); 25.06 (t); 20.99 (q); 15.78 (q)

$^1$H-NMR: 7.20 (m, 4H); 5.72 (m, 1H); 3.65 (t, J=7 Hz, 2H); 2.32 (s, 3H); 2.27 (q, J=7 Hz, 2H); 2.02 (s, 3H); 1.83 (broad s, 1H); 1.70 (t, J=7 Hz, 2H)

(4E)-5-(4-methylphenyl)-4-hexenal

Prepared as described for (4E)-4-methyl-5-(4-methylphenyl)-4-pentenal using the following reagents:
(4E)-5-(4-methylphenyl)-4-hexen-1-ol: 2.13 g (0.011 mol)
PCC: 5.8 g (0.022 mol)
Sodium acetate: 2 g The product was purified by column chromatography on silica gel (eluting with heptane/ethyl acetate 5:1) followed by bulb-to-bulb distillation. 1.4 g of the desired aldehyde was obtained (0.0075 mol; 67% yield).
B.p.=100-120° C./0.001 mbar $^{13}$C-NMR: 202.05 (s); 140.58 (s); 136.50 (s); 136.17 (s); 128.90 (d); 125.51 (d); 124.88 (d); 43.73 (t); 21.54 (t); 21.00 (q); 15.88 (q)

$^1$H-NMR: 9.80 (m, 1H); 7.18 (m, 4H); 5.68 (m, 1H); 2.60-2.48 (m, 4H); 2.32 (s, 3H); 2.02 (s, 3H)

3-methyl-2-(4-methylphenyl)-3-buten-2-ol

Prepared as described for 2-methyl-1-(3-methylphenyl)-2-propen-1-ol using the following reagents:
p-methylacetophenone 70.6 g (0.5 mol)
isopropenyl magnesium bromide (0.5 N in THF; 800 ml; 0.4 mol).

The product was purified by column chromatography on silica gel (heptane/ethyl acetate 10:1 to 5:1) followed by bulb-to-bulb distillation. 20.2 g of desired product were obtained (94% pure; 0.108 mol; 27% yield).
B.p.=81° C./0.001 mbar $^{13}$C-NMR: 150.30 (s); 143.06 (s); 136.42 (s); 128.81 (d); 125.19 (d); 110.42 (t); 76.75 (s); 28.56 (q); 20.98 (q); 19.13 (q)

$^1$H-NMR: 7.22 (m, 4 H); 5.18 (m, 1 H); 4.92 (m, 1 H); 2.32 (s, 3 H); 2.00 (s, 1 H); 1.66 (s, 3 H); 1.60 (s, 3 H)

(Z)-4-methyl-5-p-tolylhex-4-enal

Prepared as described for (4E)-4-methyl-5-(3-methylphenyl)-4-pentenal using the following reagents:
3-methyl-2-(4-methylphenyl)-3-buten-2-ol: 19 g, 0.108 mol)
Tri(ethyleneglycol)divinyl ether (22.2 g; 0.108 mol)
Hg(II) acetate (1.05 g; 0.0032 mol)

The product was purified by column chromatography on silica gel (eluting with heptane/ethyl acetate 10:1 to 2:1), followed by bulb-to-bulb distillation. 2.4 g of the desired product were obtained as a 79:17 mixture of Z/E isomers (97% chemically pure; 0.012 mol; 11% yield).
B.p.=85° C./0.001 mbar $^{13}$C-NMR (data for the major isomer): 202.57 (s); 141.77 (s); 135.64 (s); 132.68 (s); 128.98 (d); 128.75 (s); 127.86 (d); 42.77 (t); 27.99 (t); 21.40 (q); 21.08 (q); 17.67 (q)

$^1$H-NMR (data for the major isomer): 9.57 (t, J=2.5 Hz, 1H); 7.04 (m, 4H); 2.40 (m, 2H); 2.32 (m, 3H); 2.25 (m, 2H); 1.92 (s, 3H); 1.76 (s, 3H)

4-methyl-5-phenyl-4-hexenal

Prepared as described for (Z)-4-methyl-5-p-tolylhex-4-enal using the following reagents:

3-Methyl-2-phenyl-but-3-en-2-ol (J. A. Marco et al., Tetrahedron 2003, 59, 4085) (9 g, 0.055 mol)
   Tri(ethyleneglycol)divinyl ether (11.1 g; 0.055 mol)
   Mercury(II) acetate (0.57 g; 0.00018 mol)

The product was purified by column chromatography on silica gel (eluting with cyclohexane/ethyl acetate 19:1 to 9:1), followed by bulb-to-bulb distillation 140-150° C. at 4.5 mbar. 0.70 g of the desired product were obtained as a 38:62 mixture of Z/E isomers (95% chemically pure; 0.012 mol; 7% yield).

$^{13}$C-NMR: 202.6, 202.3 (s), 144.8, 144.7, 134.9, 133.7, 132.8 (s), 128.3, 128.2, 128.1, 127.9, 126.2, 126.0 (d), 42.7, 42.4 (t), 27.9, 26.8 (t), 21.4, 20.6, 19.6, 17.7 (q).

$^1$H-NMR: 9.85 (major, t, J=1.5, 1H), 9.57 (minor, t, J=2, 1H), 7.39-7.05 (m, 5H), 2.64-2.58 (major, m, 2H), 2.55-2.49 (major, m, 2H), 2.43-2.37 (minor, m, 2H), 2.25 (minor, t, J=7.4, 2H), 1.97 (major, bs,3H), 1.93 (minor, q, J=1.0, 3H), 1.78 (minor, q, J=1.0, 3H), 1.56 (major, q, J=1.1, 3H)

(E)-4-methyl-5-p-tolylpent-4-enenitrile (4E)-4-methyl-5-(4-methylphenyl)-4-pentenal (3.2 g, 0.017 mol) and hydroxylamine hydrochloride (1.77 g, 0.025 mol) were heated together in 95% ethyl alcohol (55 ml) at reflux for 4 hours. After cooling to room temperature, ethanol was removed on the rotavapor. The residue was stirred in diethyl ether (250 ml) for 30 minutes. The solid was filtered off, rinsed with diethyl ether and discarded. The filtrate was evaporated under vacuum. The product was purified by column chromatography on silica gel (eluent: heptane/ethyl acetate 11:1) followed by bulb-to-bulb distillation. 2.18 g of the desired compound were obtained (0.012 mol, 70% yield).

B.p.=80° C./0.001 mbar $^{13}$C-NMR: 136.19 (s); 134.57 (s); 133.75 (s); 128.85 (d); 128.77 (d); 127.49 (d); 119.28 (s); 35.89 (t); 21.12 (q); 17.33 (q); 16.36 (t)

$^1$H-NMR: 7.13 (s, 4H); 6.32 (b.s, 1H); 2.52-2.43 (m, 4H); 2.32 (s, 3H); 1.86 (s, 3H)

(4Z)-4-methyl-5-(4-methylphenyl)-4-pentenal

This isomer was isolated from top fractions of the distillation of (4E)-4-methyl-5-(4-methylphenyl)-4-pentenal by preparative gas phase chromatography.

$^{13}$C-NMR: 201.96 (d), 136.06 (s), 135.89 (s), 135.00 (s), 128.95 (d), 128.37 (d), 126.94 (d), 42.25 (t), 24.94 (t), 23.67 (q), 21.10 (q).

$^1$H-NMR: 9.71 (s, 1H), 7.11 (d, J=7.8 Hz, 2H), 7.05 (d, J=7.8 Hz, 2H), 6.31 (s, 1H), 2.55 (s, 4H), 2.32 (s, 3H), 1.85 (s, 3H).

Example 2

Preparation of a Perfuming Composition

An eau de cologne for man, of the musky-herbaceous type, was prepared by admixing the following ingredients:

| Ingredient | Parts by weight |
| --- | --- |
| Carbinol acetate | 50 |
| 10* Cis-3-Hexenol acetate | 20 |
| Citronellyl acetate | 20 |
| Linalyl acetate | 350 |
| 10%* Isoeugenyl acetate | 40 |
| 16-Hexadecanolide | 10 |
| 10%* Methyl anthranilate | 40 |
| Cetalox ® [1] | 10 |

-continued

| Ingredient | Parts by weight |
| --- | --- |
| 10%* Cis-3-Hexenol | 20 |
| 10%* Citral | 30 |
| Coumarine | 10 |
| 10%* Damascone Alpha | 20 |
| Dihydromyrcenol | 400 |
| 10%* Damascone Beta | 20 |
| Floralozone[2] | 25 |
| 70%** Galaxolide ® [3] | 600 |
| Geranium essential oil | 5 |
| Hedione ® [4] HC | 160 |
| Helvetolide ® [5] | 80 |
| Iso E Super ® [6] | 200 |
| Lavender essential oil | 50 |
| Lilial ® [7] | 200 |
| 10%* Methylnaphthylcetone | 20 |
| Mousse Cristal | 40 |
| Romandolide ® [8] | 500 |
| Amyl salicylate | 60 |
| Benzyl salicylate | 100 |
| Cis-3-Hexenol salicylate | 200 |
| Tonalide ® [9] | 200 |
| 10%* 2,4-Dimethyl-3-cyclohexene-l-carbaldehyde | 20 |
| | 3500 |

*in dipropyleneglycol
**in isopropyle myristate
[1] 8,12-epoxy-13,14,15,16-tetranorlabdane; origin: Firmenich SA, Geneva, Switzerland
[2] 3-(4/2-ethylphenyl)-2,2-dimethylpropanal; origin: International Flavors & Fragrances, USA
[3] 1,3,4,6,7,8-hexahydro-4,6,6,7,8,8-hexamethyl-cyclopenta-g-2-benzopyrane; origin: International Flavors & Fragrances, USA
[4] methyl cis-dihydrojasmonate; origin: Firmenich SA, Geneva, Switzerland
[5] (1S,1'R)-2-[1-(3',3'-dimethyl-1'-cyclohexyl)ethoxy]-2-methylpropyl propanoate; origin: Firmenich SA, Geneva, Switzerland
[6] 1-(octahydro-2,3,8,8-tetramethyl-2-naphtalenyl)-1-ethanone; origin: International Flavors & Fragrances, USA
[7] 3-(4-tert-butylphenyl)-2-methylpropanal; origin: Givaudan SA, Geneva, Switzerland
[8] (1S,1'R)-[1-(3',3'-dimethyl-1'-cyclohexyl)ethoxycarbonyl]methyl propanoate; origin: Firmenich SA, Geneva, Switzerland
[9] (5,6,7,8-tetrahydro-3,5,5,6,8,8-hexamethyl-2-naphtyl)-1-ethanone; origin: Givaudan SA, Geneva, Switzerland When there were added 200 parts by weight of (4E)-4-methyl-5-(4-methylphenyl)-4-pentenal to the above-described eau de cologne, then the new fragrance acquired a body and a powdery-mimosa/lily of the valley sweetness which is very cosmetic, it brings to the eau de cologne also a nursing aspect.

When instead of the above invention's compound there was added the same amount of (4E)-2,4-dimethyl-5-(4-methylphenyl)-4-pentenal, then the new fragrance became more green, more anisic.

The addition to the original eau de cologne of the same amount of Mefranal® provided a new fragrance which acquired a clear citrus, citronella character.

Example 3

Preparation of a Perfuming Composition

A cologne, of the floral-watery type, was prepared by admixing the following ingredients:

| Ingredient | Parts by weight |
| --- | --- |
| 10%* Phenylacetic aldehyde | 20 |
| 16-Hexadecanolide | 40 |
| Dihydro Beta Ionone | 350 |
| 7-Methyl-2H,4H-1,5-benzodioxepin-3-one | 80 |
| Citronellol | 300 |
| Allyl (cyclohexyloxy)-acetate | 20 |
| Decal | 20 |
| Dimetol ® [1] | 20 |
| 10%* Ethylvanilline | 100 |
| Eugenol | 80 |

-continued

| Ingredient | Parts by weight |
|---|---|
| Exaltolide® [2] | 360 |
| 70%** Galaxolide® [3] | 2200 |
| Hedione® [4] | 1000 |
| 10%* Indol | 150 |
| Beta Ionone | 20 |
| Iso E Super® [5] | 1300 |
| Lilial® [6] | 1150 |
| Linalool | 270 |
| Lyral® [7] | 250 |
| 10%* 2,6-Dimethyl-5-heptanal | 50 |
| Paradisone® [8] | 100 |
| Phenethylol | 70 |
| 10%* 2,4-Dimethyl-3-cyclohexene-1-carbaldehyde | 50 |
| | 8000 |

*in dipropyleneglycol
**in isopropyle myristate
[1] 2,6-dimethyl-2-heptanol; origin: Givaudan SA, Geneva, Switzerland
[2] pentadecanolide; origin: Firmenich SA, Geneva, Switzerland
[3] 1,3,4,6,7,8-hexahydro-4,6,6,7,8,8-hexamethyl-cyclopenta-g-2-benzopyrane; origin: International Flavors & Fragrances, USA
[4] methyl dihydrojasmonate; origin: Firmenich SA, Geneva, Switzerland
[5] 1-(octahydro-2,3,8,8-tetramethyl-2-naphtalenyl)-1-ethanone; origin: International Flavors & Fragrances, USA
[6] 3-(4-tert-butylphenyl)-2-methylpropanal; origin: Givaudan SA, Geneva, Switzerland
[7] 4/3-(4-(hydroxy-4-methylpentyl)-3-cyclohexene-1-carbaldehyde; origin: International Flavors & Fragrances, USA
[8] (+)-methyl (1R)-cis-3-oxo-2-pentyl-1-cyclopentaneacetate; origin: Givaudan SA, Geneva, Switzerland When there were added 300 parts by weight of (4E)-4-methyl-5-(4-methylphenyl)-4-pentenal to the above-described eau de cologne, then it was obtained a new cologne having a considerably reinforced watery aspect going with a nice floral-lily of the valley and powdery-mimosa note. When instead of the above invention's compound there was added the same amount of (4E)-2,4-dimethyl-5-(4-methylphenyl)-4-pentenal, then the new cologne, compared to the one obtained by the addition of (4E)-4-methyl-5-(4-methylphenyl)-4-pentenal, became more linden/verbena and acquired also a slightly almond aspect.

The addition to the original eau de cologne of the same amount of Mefranal® provided a new fragrance which acquired a clear citrus, citronella character.

Example 4

Preparation of a Perfuming Composition

A perfuming composition for a fabric softener was prepared by admixing the following ingredients:

| Ingredient | Parts by weight |
|---|---|
| Benzyl acetate | 150 |
| Carbinol acetate | 50 |
| Anisic aldehyde | 80 |
| 10%* C 12 Aldehyde | 40 |
| 10%* C 8 Aldehyde | 20 |
| Hexylcinnamic aldehyde | 150 |
| 10%* MNA Aldehyde | 30 |
| Methyl anthranilate | 40 |
| 10%* Ethyl 2-methylpentanoate | 40 |
| Undecalactone Gamma | 50 |
| Benzophenone | 10 |
| Cetalox® [1] | 40 |
| Lemon essential oil | 50 |
| Citronellol | 150 |
| 4-Cyclohexyl-2-methyl-2-butanol | 220 |
| Verdyl propionate | 100 |
| Coumarine | 150 |
| 3-(4-Isopropylphenyl)-2-methylpropanal | 20 |
| Damascone Alpha | 10 |

| Ingredient | Parts by weight |
|---|---|
| (1'R,E)-2-Ethyl-4-(2',2',3'-trimethyl-3'-cyclopenten-1'-yl)-2-buten-1-ol [2] | 50 |
| Dihydromyrcenol | 120 |
| Ethylvanilline | 20 |
| Habanolide® [3] | 100 |
| Heliotropine | 50 |
| Iralia® [4] Total | 120 |
| Lilial® [5] | 200 |
| Isopropyl methylbutyrate | 10 |
| Methylnaphthylketone | 30 |
| 10%* Mousse Cristal | 60 |
| Muscenone [6] Delta | 20 |
| Hedione® [7] | 250 |
| 10%* Neobutenone® [8] Alpha | 10 |
| Nirvanol® [9] | 30 |
| Patchouli essential oil | 20 |
| Peonile® [10] | 200 |
| Phenethylol | 250 |
| Phenylhexanol | 450 |
| Orange essential oil | 50 |
| Hexyle salicylate | 50 |
| Benzyl salicylate | 200 |
| Terpineol | 50 |
| Tetralinol | 200 |
| Undecavertol | 20 |
| Yara Yara | 20 |
| 2,4-Dimethyl-3-cyclohexene-1-carbaldehyde | 20 |
| | 4000 |

*in dipropyleneglycol
[1] 8,12-epoxy-13,14,15,16-tetranorlabdane; origin: Firmenich SA, Geneva, Switzerland
[2] origin: Firmenich SA, Geneva, Switzerland
[3] pentadecanolide; origin: Firmenich SA, Geneva, Switzerland
[4] mixture of methyl ionones; origin: Firmenich SA, Switzerland
[5] 3-(4-tert-butylphenyl)-2-methylpropanal; origin: Givaudan-Roure SA, Vernier, Switzerland
[6] 3-methyl-(4)-cyclopentadecenone; origin: Firmenich SA, Switzerland
[7] methyl dihydrojasmonate; origin: Firmenich SA, Switzerland
[8] 1-(5,5-dimethyl-1-cyclohexen-1-yl)-4-penten-1-one; origin: Firmenich SA, Switzerland
[9] 3,3-dimethyl-5-(2,2,3-trimethyl-3-cyclopenten-1-yl)-4-penten-2-ol; origin: Firmenich SA, Switzerland
[10] cyclohexylidene(phenyl)acetonitrile; origin: Givaudan-Roure SA, Vernier, Switzerland When there were added 100 parts by weight of (4E)-4-methyl-5-(4-methylphenyl)-4-pentenal to the above-described perfume, then the new fragrance acquired spectacular character due to a floral sweetness, as well as a watery and powdery aspect. The effect was clearly perceivable on a wet or dry fabric washed treated with a softener containing said fragrance. The effect provided by the invention's compound was much less chemical than the one obtained with anisic aldehyde, and was much more sweet-floral than the one obtained by using the known ingredients 3-(4-methoxyphenyl)-2-methylpropanal or 3-(1,3-benzodioxol-5-yl)-2-methylpropanal.

When instead of the above invention's compound there was added the same amount of (4E)-2,4-dimethyl-5-(4-methylphenyl)-4-pentenal, then the new fragrance, compared to the one obtained by the addition of (4E)-4-methyl-5-(4-methylphenyl)-4-pentenal, became more aldehydic with a connotation of the anis-linden type.

The addition to the original eau de cologne of the same amount of Mefranal® provided a new fragrance which acquired a clear citrus, citronella character.

What is claimed is:

1. A compound of formula

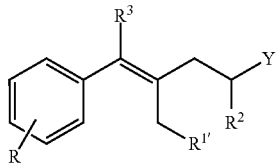

(II)

wherein:
- R<sup>1'</sup> represents a hydrogen atom or a methyl group;
- Y represents a $CH_2OH$ group or a group X;
- R is an ortho, meta or para substituent of the phenyl, and represents a $C_{1-2}$ alkyl or alkoxyl group;
- $R^2$ represents a hydrogen atom or a methyl or ethyl group;
- $R^3$ represents a hydrogen atom or a methyl or ethyl group; and
- X represents a CHO group; and
- said compound being in the form of a E or Z isomer or of a mixture thereof, and wherein said compound provides lily of the valley and powdery-anis fragrance notes.

2. A compound according to claim 1, wherein the compound (II) is one wherein R is a methyl group, $R^2$ or $R^3$ represents a hydrogen atom or methyl group, and R<sup>1'</sup> represents a hydrogen atom.

3. A compound according to claim 1, wherein the compound (II) is (4E)-4-methyl-5-(4-methylphenyl)-4-pentenal or (4E)-2,4-dimethyl-5-(4-methylphenyl)-4-pentenal.

4. The compound according to claim 1, wherein R is a methyl group, $R^2$ or $R^3$ represents a hydrogen atom or methyl group, and R<sup>1'</sup> represents a methyl group.

5. The compound according to claim 1, wherein:
- R is a methyl group;
- R<sup>1'</sup> represents a hydrogen atom;
- $R^2$ represents a hydrogen atom or a methyl group; and
- $R^3$ represents a hydrogen atom.

6. A composition comprising a compound according to claim 1, wherein the composition is selected from the group consisting of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach, wherein the compound is present in an amount sufficient to impart thereto lily of the valley and powdery-anis fragrance notes.

7. A composition comprising a compound according to claim 2, wherein the composition is selected from the group consisting of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach, wherein the compound is present in an amount sufficient to impart thereto lily of the valley and powdery-anis fragrance notes.

8. A composition comprising a compound according to claim 3, wherein the composition is selected from the group consisting of solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach, wherein the compound is present in an amount sufficient to impart thereto lily of the valley and powdery-anis fragrance notes.

9. A composition comprising a compound according to claim 4, wherein the composition is selected from the group consisting of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach, wherein the compound is present in an amount sufficient to impart thereto lily of the valley and powdery-anis fragrance notes.

10. A composition comprising a compound according to claim 5, wherein the composition is selected from the group consisting of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach, wherein the compound is present in an amount sufficient to impart thereto lily of the valley and powdery-anis fragrance notes.

* * * * *

UNITED STATES PATENT AND TRADEMARK OFFICE
CERTIFICATE OF CORRECTION

PATENT NO.        : 9,487,734 B2
APPLICATION NO.   : 14/323594
DATED             : November 8, 2016
INVENTOR(S)       : Moretti Page 1 of 1

It is certified that error appears in the above-identified patent and that said Letters Patent is hereby corrected as shown below:

In the Claims

Column 23:
Line 35 (Claim 4, Line 3), delete "$R^{1}$" and insert -- $R^{1'}$ --.

Column 24:
Line 17 (Claim 8, Line 3), after "consisting of", insert -- a --.

Signed and Sealed this
Third Day of January, 2017

Michelle K. Lee
*Director of the United States Patent and Trademark Office*